United States Patent
Baars et al.

(10) Patent No.: US 8,091,408 B2
(45) Date of Patent: Jan. 10, 2012

(54) PROCEDURE FOR OPERATING A COLLECTING PARTICLE SENSOR AND DEVICE FOR IMPLEMENTING THIS PROCEDURE

(75) Inventors: Enno Baars, Leonberg (DE); Harald Koehnlein, Stuttgart (DE); Thomas Marc Kammerer, Mandelbachtal (DE); Bernhard Kamp, Ludwigsburg (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 486 days.

(21) Appl. No.: 12/052,496

(22) Filed: Mar. 20, 2008

(65) Prior Publication Data
US 2009/0019918 A1  Jan. 22, 2009

(30) Foreign Application Priority Data
Mar. 28, 2007  (DE) .......................... 10 2007 014 761

(51) Int. Cl.
*G01N 7/00* (2006.01)
(52) U.S. Cl. ...................................... 73/23.31
(58) Field of Classification Search .................. 73/23.31, 73/23.33, 204.17
See application file for complete search history.

(56) References Cited

U.S. PATENT DOCUMENTS

| | | | |
|---|---|---|---|
| 6,845,660 B2 * | 1/2005 | Hecht et al. | ................ 73/204.17 |
| 7,587,925 B2 * | 9/2009 | Wirth et al. | ................. 73/23.33 |
| 2003/0196499 A1 * | 10/2003 | Bosch et al. | ................. 73/865.5 |

FOREIGN PATENT DOCUMENTS

| DE | 101 33 285 | 8/2002 |
|---|---|---|
| DE | 101 33 384 | 1/2003 |

* cited by examiner

*Primary Examiner* — Hezron E Williams
*Assistant Examiner* — Tamiko D Bellamy
(74) *Attorney, Agent, or Firm* — Merchant & Gould P.C.

(57) ABSTRACT

A procedure for operating a collecting particle sensor, which is provided with measuring phases, during which particles that are contained in an off-gas stream accumulate on a measuring route, and a device for implementing this procedure are submitted. Protection phases are provided, during which at least one measure for diminishing the accumulation of particles on the measuring route is adopted. The measure according to this invention prevents a decrease of the sensitivity of the particle sensor over a long period of time.

12 Claims, 1 Drawing Sheet

PROCEDURE FOR OPERATING A COLLECTING PARTICLE SENSOR AND DEVICE FOR IMPLEMENTING THIS PROCEDURE

TECHNICAL FIELD

The invention is based on a procedure for operating a collecting particle sensor and on a device for implementing this procedure according to the category of the independent claims. Subject matter of the invention is furthermore a control program as well as a control program product.

BACKGROUND

For controlling and if necessary regulating the combustion features during combustion processes there is a demand for a detection of at least one dimension for the particle concentration in the exhaust gas. There is especially a demand for detecting at least one dimension for the particle concentration in the exhaust gas of combustion engines, specifically of diesel combustion engines.

The term particle concentration equally faces a particle mass or a particle amount in the following. It will be referred to a particle mass only. The particle mass related to the time can be of interest. As long as the combustion process occurs in a combustion engine, which is arranged in a motor vehicle, the particle mass, which has accrued on a specific route, can be of interest.

In DE 101 33 285 A1 a particle sensor is described that contains a collecting chamber, which can be exposed to an off-gas stream. A first electrode is arranged on the top of the collecting chamber. A second electrode is arranged on the bottom, oppositely of the first electrode. The collecting chamber is hollow between both electrodes. During the operation of the sensor particles, especially soot particles, get into the collecting chamber and embed in the hollow between the two electrodes. The particles that are at least slightly electrically conductive bridge the gap between the two electrodes, so that the impedance of the sensor route of the particle sensor changes. The impedance or the timely change of the impedance, which are a measurement for the loading or the increase of the loading of the particle sensor with particles, can be evaluated. Since the measuring effect is based on an accumulation of particles, the particles sensor can be referred to as a collecting particle sensor.

In DE 101 33 384 A1 a further particle sensor described, at which the two electrodes intertwine comb-like. The impedance and/or the change between the two electrodes can also be used for this collecting particle sensor at least as a measurement for the particle mass in the exhaust gas, which occurred in a preset time and/or based on a route.

On the basis of experiments it turned out that the known collecting particle sensors, for example resistive particle sensors, show cross sensitivities, which can lead to an influencing of the measuring signal at a change of the conditions of the combustion process. Furthermore it turned out that the sensitivity of the particle sensor can be influenced by different substances in such a way that the sensitivity decreases towards the particles that have to be measured.

The invention is based on the assignment to provide a procedure for operating a particle sensor and a device for implementing this procedure, at which the measuring signal reflects a measurement as accurate as possible during the entire operating time for the particles that have to be detected.

This assignment is solved by the characteristics that are listed in the independent claims.

SUMMARY

The procedure according to the invention has the advantage that the particle sensor shows during the entire operating time at least approximately a constantly high measuring accuracy.

It is proceeded on the assumption that a collecting particle sensor, which has additionally to one measuring phase a protection phase, during which at least one action for decreasing the accumulation of substances on the measuring route of the particle sensor is taken. Thereby it can be worked against the contamination of the measuring route.

A contamination of the particle sensor can be understood as any influencing of the measuring signal, which is not caused by the particles that have to be detected. For example a cross sensitivity towards hydrocarbons and/or water can be present. Especially the ash of the combustion process, which has been condensed on the measuring route of the particle sensor and which cannot be eliminated by free-burning in the regenerating phases, leads to a constant decrease of the sensitivity of the particle sensor towards the particles that have to be detected.

The decrease of the contamination of the measuring route of the particle sensor ensures a constant sensitivity towards the particles that have to be detected over a long period of time.

Advantageous embodiments and improvements of the procedure according to the invention arise from dependent claims.

A first action for decreasing the accumulation of substances during the protection phase provides for an operating voltage that is applied to the measuring route to be minimized towards a rated operating voltage that has been preset during a measuring phase. The decrease of the operating voltage, which is completely turned off according to one embodiment, minimizes the gravitation that results from the electrical field towards electrically charged substances, which are contained in the exhaust gas and which pass by the measuring route on the one hand. On the other hand the polarizing effect towards the electrically not charged substances in the exhaust gas is decreased, so that an electric gravitation cannot even develop at all.

Another action, which can be provided alternatively or additionally, provides for a relation between the measuring route during the protection phase, whereby the temperature is set to a value that lies above the exhaust gas temperature. Appropriate is such a temperature that is approximately 50 degrees Celsius to 150 degrees Celsius above the current exhaust gas temperature. With this action a temperature gradient starting from the surface of the measuring route to the exhaust gas is built, which causes a thermophoretic effect, which works against an accumulation of substances from the off-gas stream on the measuring route.

One embodiment provides that the heating of the measuring route during the protection phase is only enabled if a dew point signal is present, which signalizes that a moisture condensation can occur at least in the area of the measuring route of the particle sensor, and as the case may be in the entire area of the particle sensor. Thereby a damage of the particle sensor's ceramic by a thermal shock can be avoided.

As long as the particle sensor is only turned on for a comparatively short time, only a short time maybe available for the protection phase. According to one embodiment it is therefore provided that the quantity of starting up the particle sensor is determined in relation to its operating time, and that in the case of exceeding a start-up-frequency-threshold the measuring phase is disabled and instead the protection phase is preset.

Another embodiment provides that the protection phase of a particle sensor that is arranged in the exhaust gas area of a combustion engine is provided only in preset operating status areas of the combustion engine and/or in preset exhaust gas parameter areas. A quasi-stationary operating status for example, in which the change of the engine speed or a change of the load of the combustion engine lies within a designated area, is appropriate. If necessary a checking whether the load of the combustion engine lies underneath a load threshold is provided. Appropriate is furthermore a status, at which the exhaust gas temperature lies underneath an exhaust gas temperature threshold.

The device for implementing this procedure according to the invention is initially based on a control unit that has been specifically customized for the implementation of the invention. The control unit contains preferably at least one electronic storage, in which the procedure steps are saved as a control program.

According to the invention the control program provides that all steps of the procedure according to the invention are implemented if it takes place in a control unit.

According to the invention the control program product with a program code that is saved on a machine-readable medium performs the procedure if the program takes place in a control unit.

Further advantageous improvements and embodiments of the invention's procedure arise from further dependent claims. Examples of embodiments are shown in the drawing and specified in the following description.

DETAILED DESCRIPTION

Figure 1:
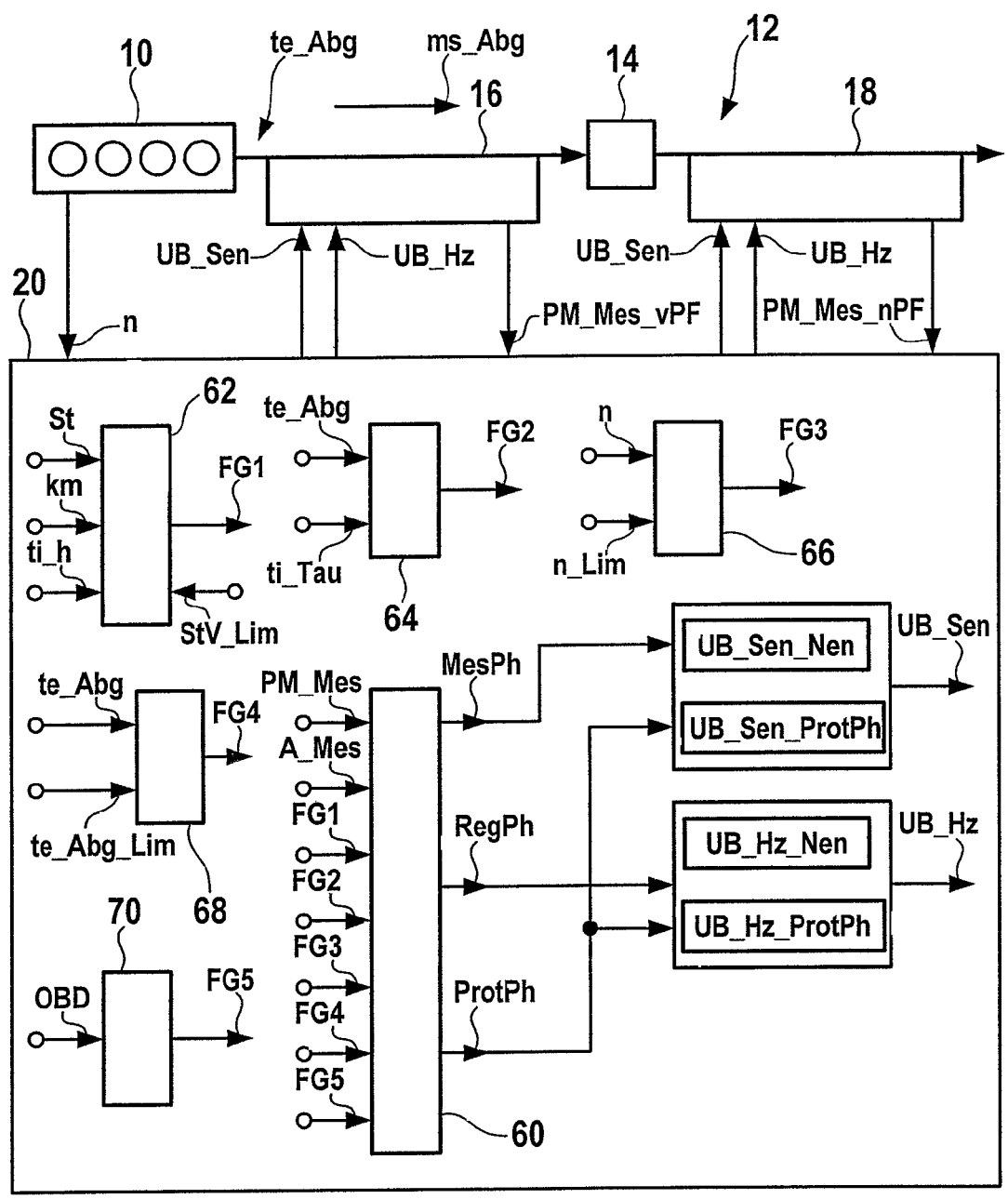
FIG. 1 is a technical environment, in which according to the invention a procedure for operating an integrated particle sensor takes place

FIG. 1 shows a combustion engine 10, in whose exhaust gas area 12 a particle filter 14 is arranged. In the exhaust gas area 12 an exhaust gas mass flow ms_Abg appears, which shows an exhaust gas temperature te_Abg.

An upstream particle sensor 16 is arranged upstream before the particle filter 14 and a downstream particle sensor 18 downstream after the particle filter 14. The upstream particle sensor 16 provides an upstream measuring signal PM_Mes_vPF for a control unit 20 and the downstream particle sensor 18 a downstream measuring signal PM_Mes_nPF. These signals are referred to as measuring signal PM_Mes in the following. The control unit 20 provides a sensor heating operating voltage Ub_Hz as well as a measuring route operating voltage Ub_Sen for the particle sensors 16, 18.

The combustion engine 10 provides the engine speed n for the control unit.

An embodiment provides that in the exhaust gas area 12 of the combustion engine 10 as an example for a combustion process at least one particle sensor 16, 18 is arranged. The upstream particle sensor 16 can be provided in order to detect the particle emissions of the combustion engine 10, which are present in the off-gas stream ms_Abg. The downstream particle sensor 18, which can be provided alternatively or additionally, detects the particles that are present in the exhaust gas stream flow ms_Abg downstream after the particle filter 14 and allows thereby especially a diagnosis of the particle filter 14.

Figure 2:
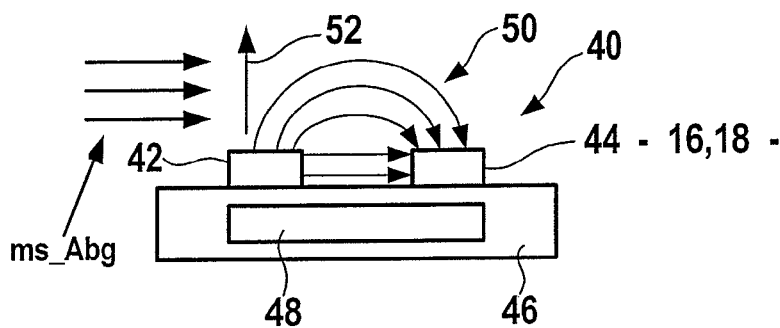
FIG. 2 is a cross-section in the area of a measuring route of a particle sensor.

FIG. 2 shows a cross-section in the area of a measuring route 40 of the particle sensor 16, 18. The measuring route 40 is build by a gap between at least a first electrode 42 as well as an adjacent second electrode 44. Preferably several electrodes 42, 44 are provided, in between which the measuring routes 40 are located. The electrodes 42, 44 are preferably arranged on a ceramic substrate 46, which contains preferably a sensor heating 48, with which the measuring route 40 can be heated.

The electrodes 42, 44 are impinged with the measuring route operating voltage Ub_Sen, while the sensor heating operating voltage Ub_Hz is provided for the sensor heating 48.

The sensor route 40 of the particle sensor 16, 18 is exposed to the exhaust gas mass flow ms_Abg. In the displayed embodiment it is proceeded from the fact that the sensor route 40 is arranged at least parallel to the exhaust gas mass flow ms_Abg. At least one part of the substances that are contained in the exhaust gas mass flow ms_Abg, which are not gaseous, can accumulate on the measuring route 40.

The accumulation can be specifically influenced on the one hand by the measuring route operating voltage Ub_Sen and on the other hand by the determination of the sensor heating operating voltage Ub_Hz.

Electrically charged substances in the exhaust gas mass flow ms_Abg, which is referred to as off-gas stream in the following, are drawn in the direction of the measuring route 40 at an applied measuring route operating voltage Ub_Sen due to the electrical gravity caused by the electrical field 50 outgoing from the electrodes 42, 44. Electrically uncharged substances in the off-stream gas ms_Abg can be polarized due to the electrical field 50, so that an electrical gravity also accrues, which drives the substances in the direction of the measuring route 40. This effect can be referred to as electrophoresis.

Depending on the temperature of the measuring route 40, which can be varied by the sensor heating operational voltage Ub_Hz or by the heat output of the sensor heating 48, a temperature gradient 52 occurs between the measuring route 40 and the off-stream gas ms_Abg. Due to the thermophoretic effect a particle flow towards the temperature gradient 52 occurs, whereby it is proceeded according to the embodiment in FIG. 2 from the fact that the temperature of the sensor route 40 is higher than the temperature of the exhaust gas mass flow ms_Abg, so that the temperature gradient 52 shows away from the measuring route 40 and thereby the particle flow is directed away from the measuring route 40.

The at least one particle sensor 16, 18 is build as a collecting particle sensor 16, 18, whose measuring signal PM_Mes, PM_Mes_vPF, PM_Mes_nPF is a dimension for the particles, which have been collected over a preset time and which have condensed on the measuring route 40. The measuring effect is based for example on an evaluation of the capacitive characteristics of the measuring route 40, which are altered by the particles that have to be detected. Preferably a resistive procedure is provided, during which the impendence, preferably only the resistive part of the impendence is evaluated, which shows particles that have condensed on the measuring route 40. If a threshold is reached, the measuring route 40 of the particle sensor 16, 18 is heated with the aid of the sensor heating 48 up to a temperature, at which a free-burning of the measuring route 40 of the particles that have condensed and that have to be detected, occurs. Normally it is a matter of soot particles, which show, without any further conditioning, an ignition temperature, which lies in the area of 550 degrees Celsius to 650 degrees Celsius. The required temperature is referred to as free-burning temperature.

During the operating of the particle sensor 16, 18 further particles contained in the off-stream gas ms_Abg can condense on the measuring route 40 in addition to those that have to be detected, which leads to a falsification of the measuring signal PM_Mes, PM_Mes_vPF, PM_Mes_nPF on the one hand and generally it can lead to a decrease of the sensitivity of the particle sensor 16, 18 on the other hand. These substances can be for example the hydrocarbons contained in the exhaust gas mass flow ms_Abg or for example water. Generally these substances can be removed during the regeneration phase, during which the measuring route 40 is heated up to a free-burning temperature. These substances can especially be the ashes contained in the off-gas stream ms_Abg, which emerge for example from the combustion of oil. The ash leads to a contamination of the measuring route 40, which results in an advancing decline of the sensitivity of the particle sensor 16, 18, since the ash cannot be removed during the regeneration phase.

According to the invention it is therefore provided that additionally to the measuring phases protection phases are provided, during which at least one measure is adopted, which declines the accumulation of substances on the measuring route 40 of the particle sensor 16, 18.

The controller 20 contains a particle sensor control unit 60, which provides a measuring phase MesPh, a regeneration phase RegPh and a protection phase ProtPh depending on the measuring signal PM_Mes, depending on a measuring demand A_Mes and depending on clearance signals FG1-FG5.

A first measure that is adopted during a protection phase ProtPh is the lowering of the sensor route operating voltage Ub_Sen, which is declined during a protection phase ProtPh from a rated operating voltage Ub_Sen_Nen on to a protection phase operating voltage Ub_Sen_ProtPh. According to an embodiment the sensor route operating voltage Ub_Sen can be completely turned off. By the decrease or complete turning-off of the sensor route operating voltage Ub_Mes the electrical field 50 diminishes or drops completely, which is responsible for the attractivity of electrically charged particles that are contained in the exhaust gas or for their polarization and following attractivity towards the measuring route 40.

An alternative or additional measure provides that the sensor heating 48 is turned on during the protection phase ProtPh, whereby the protection phase heating operating voltage Ub_Hz_ProtPh is set to a preferably lower value than during the regeneration phase RegPh, in which the sensor heating operating voltage is set to a free-burning operating voltage Ub_Hz_Nen. A temperature rise by about 50 degrees Celsius to 150 degrees Celsius towards the actual exhaust gas temperature te_Abg is applicable. Altogether the sensor temperature during the protection phase should lie under the free-burning temperature, so that the heating of the particle sensor 16, 18 can be carried out with a comparatively low consumption of energy. With this measure it is attempted to use the thermophoretic effect during the protection phase ProtPh so that a substance transport along the temperature gradient 52 towards the off-gas stream ms_Abg away from the sensor route 40 occurs and that the accumulation of substances on the sensor route 40 is diminishes or completely prevented.

The particle sensor controller 60 can induce or suppress the measuring phases MesPh, the regeneration phases RegPh and the protection phases ProtPh depending on several clearance signals FG1-FG2.

A first clearance signal FG1 induces the starting of the protection phase ProtPh depending on the amount of the start-ups of the particle sensor 16, 18 based on its operating time. This key number is determined in the particle sensor operating time determination 62 for example depending on the start-ups St of the particle sensor 16, 18 and depending on the following operating time ti_h. As long as a combustion engine 10 is provided as a combustion process, the start-ups of the particle sensor 16, 18 can be read from the amount of start-ups St of the combustion engine 10. Furthermore the distance km that has been covered with the motor vehicle can be considered instead of the operating time ti_h.

The key number is compared to a turning-on frequency threshold StV_Lim in the particle sensor operating time determination 62. An exceeded of the turning-on frequency threshold StV_Lim shall mean that the particle sensor 16, 18 has been in operation each time for a comparatively short operating time ti_h km and therefore has only been operated in measuring phases MesPh where required. After it can be assumed that the measuring signal PM_Mes, PM_Mes_vPF, PM_Mes_nPF was provided long enough during the measuring phases MesPh, further measurements can be abandoned, so that the particle sensor controller 60 can induce the protection phase ProtPh with the first clearance signal FG1.

A second clearance signal FG2 is provided by a dew point lower deviation determination 64. The dew point lower deviation determination 64 determines a present or at least imminent dew point lower deviation for example from the exhaust gas temperature te_Abg and a preset time ti_Tau. Not until it can be assumed with a high probability that no dew point lower deviation occurs in the area of the particle sensor 16, 18, at least in the area of the heated measuring route 40, the second clearance signal FG2 is provided, which authorizes the particle sensor controller 60 to activate the sensor heating 48 within a regeneration phase RegPh or within a protection phase ProtPh. It can alternatively be provided that without a second clearance signal FG2 the sensor heating operating voltage Ub_Hz is not completely turned off, but fixed to a value that lies during the protection phase ProtPh below the preset protection phase sensor heating operating voltage Ub_Hz_ProtPh, so that a heating of the particle sensor 16, 18 is at least started.

A third clearance signal FG3 is provided by the engine speed evaluation 66 depending on the engine speed n as an example for a key number of the combustion engine 10 by a comparison with a engine speed threshold n_Lim. Alternatively or additionally an evaluation of the load and/or the load change of the combustion engine 10 can be provided. As a dimension for the load of the combustion engine 10 a not further specified fuel signal for example can be used, which determines the fuel quantity that has to be attributed to the combustion engine 10. Additionally or alternatively the air volume or air mass that is sucked in by the combustion engine 10 can be evaluated.

A forth clearance signal FG4 is provided by a temperature evaluation 68 depending on the exhaust gas temperature te_Abg as an example for a key number of the exhaust gas by a comparison with the exhaust gas temperature threshold te_Abg Lim. The clearance signal FG4 is provided, if the actual exhaust gas temperature te_Abg is below the exhaust gas temperature threshold te_Abg_Lim.

A fifth clearance signal FG5 is provided by a diagnose controller 70 depending on a diagnose demand OBD. The diagnose demand OBD signalizes for example that a diagnosis of the particle filter 14 has to be carried out by a measuring the particles that pass the particle filter 14. For this purpose at least the downstream particle sensor 18 is necessary. When the diagnosis is completed, the diagnose controller 70 provides the fifth clearance signal FG5, which authorizes the particle sensor controller 60 to preset the regeneration phase RegPh or especially the protection phase ProtPh.

The invention claimed is:

1. A method of operating a collecting particle sensor disposed in an exhaust gas mass flow, the method comprising:
   accumulating particles contained in the exhaust gas mass flow on a measuring section of the particle sensor during a measuring phase; and
   adopting at lease one step for reducing accumulation of particles on the measuring section during a protection phase, wherein the at least one step includes presetting an operating voltage of the measuring section to a voltage value less than a nominal operating voltage of the measuring section provided during the measuring phase.

2. A method according to claim 1, further comprising turning off the operating voltage during the protection phase.

3. A method according to claim 1, further comprising heating the measuring section during the protection phase to a fixed temperature value greater than an exhaust gas temperature.

4. A method according to claim 3, wherein the fixed temperature value is at least approximately 50 degrees Celsius to 150 degrees Celsius above the exhaust gas temperature.

5. A method according to claim 3, wherein the heating of the measuring section is allowed to proceed when a clearance signal is presented, wherein the clearance signal signalizes that no moisture condensation at least in an area of the measuring section can occur.

6. A method according to claim 1, further comprising determining a number of start-ups of the particle sensor based on a particle sensor operating time, wherein the measuring phase is suppressed and the protection phase provided upon the number of particle sensor start-ups exceeding a start-up frequency threshold.

7. A method according to claim 1, wherein the protection phase is only provided at a preset operating status of a combustion engine or at a preset exhaust gas key number.

8. A method according to claim 7, wherein the protection phase is only provided with the combustion engine at a stationary operating status, wherein an engine speed change or a load change of the combustion engine lies within a preset area.

9. A method according to claim 7, wherein the protection phase is only provided if an exhaust gas temperature lies below an exhaust gas temperature threshold or a load of the combustion engine is below a load threshold.

10. A device for operating a collecting particle sensor disposed in an exhaust gas mass flow of an internal combustion engine, the device comprising at least one customized controller to implement: a measuring phase of the particle sensor wherein particles contained in the exhaust gas mass flow accumulate on a measuring section of the particle sensor; and a protection phase, wherein at least one step for diminishing accumulation of particles on the measuring section is adopted, wherein the at least one step includes presetting an operating voltage of the measuring section to a voltage value less than a nominal operating voltage of the measuring section provided during the measuring phase.

11. A device according to claim 10, wherein the customized controller contains a particle sensor controller which presets a measuring phase and the protection phase of the collecting particle sensor.

12. A method of operating a collecting particle sensor disposed in an exhaust gas mass flow, the method comprising:
    accumulating particles contained in the exhaust gas mass flow on a measuring section of the particle sensor during a measuring phase;
    evaluating an impedance resulting from particles deposited on the measuring section during the measuring phase;
    upon reaching an impedance threshold value, burning deposited particles by heating the measuring section during the measuring phase; and
    heating the measuring section during a protection phase, independent of said impedance evaluation, to a fixed temperature value greater than an exhaust gas temperature and less than a particle burn-off temperature to induce a thermophoretic effect wherein a mass effect transfer occurs along a temperature gradient and thereby accumulation of matter on the measuring section is reduced or prevented.

* * * * *